(12) United States Patent
Semsch et al.

(10) Patent No.: US 9,980,846 B2
(45) Date of Patent: May 29, 2018

(54) ORTHOSIS AND CORRECTIVE JOINT

(71) Applicant: Ortema GmbH, Markgröningen (DE)

(72) Inventors: Hartmut Semsch, Stuttgart (DE);
Gert-Peter Brueggemann, Köln (DE);
Martin Kuesel-Feldker, Köln (DE)

(73) Assignee: ORTEMA GMBH, Markgroeningen (DE)

( * ) Notice: Subject to any disclaimer, the term of this patent is extended or adjusted under 35 U.S.C. 154(b) by 436 days.

(21) Appl. No.: 14/687,846

(22) Filed: Apr. 15, 2015

(65) Prior Publication Data

US 2015/0216701 A1    Aug. 6, 2015

Related U.S. Application Data

(63) Continuation of application No. PCT/EP2013/071005, filed on Oct. 9, 2013.

(30) Foreign Application Priority Data

Oct. 16, 2012  (DE) .................. 10 2012 218 804

(51) Int. Cl.
*A61F 5/01* (2006.01)
*A61F 5/30* (2006.01)

(52) U.S. Cl.
CPC .......... *A61F 5/0123* (2013.01); *A61F 5/0102* (2013.01); *A61F 5/30* (2013.01); *A61F 2005/0174* (2013.01)

(58) Field of Classification Search
CPC ........ A61F 5/01; A61F 5/0123; A61F 5/0102; A61F 5/30; A61F 2005/0174; A61F 5/0125; A61F 2005/0139; A61F 2005/0167
See application file for complete search history.

(56) References Cited

U.S. PATENT DOCUMENTS

| | | | |
|---|---|---|---|
| 5,074,290 A * | 12/1991 | Harris | A61F 5/0123 602/16 |
| 5,586,970 A | 12/1996 | Morris et al. | |
| 7,887,496 B2 * | 2/2011 | Kahlmeyer | A61F 5/0123 16/221 |
| 2012/0143111 A1 | 6/2012 | Bledsoe | |

FOREIGN PATENT DOCUMENTS

| | | |
|---|---|---|
| DE | 600 35 431 T2 | 3/2008 |
| GB | 2 327 044 A | 1/1999 |
| WO | 2011154779 A1 | 12/2011 |

\* cited by examiner

*Primary Examiner* — Ophelia A Hawthorne
(74) *Attorney, Agent, or Firm* — Hackler Daghighian Martino & Novak

(57) ABSTRACT

An orthosis for stabilizing a joint has a joint rail having a first and a second rail portion which can be pivoted relative to each other about a joint axle. The orthosis has a pressure member which can be adjusted by a relative pivoting of the two rail portions about the joint axle in the direction towards and counter to the joint to be stabilized. One of the two rail portions has a cam disc, and the other of the two rail portions has a rotor which is guided on the cam disc, wherein the cam disc or the rotor is axially fixed in position on the correction pad.

20 Claims, 3 Drawing Sheets

ORTHOSIS AND CORRECTIVE JOINT

CROSS-REFERENCE TO RELATED APPLICATIONS

This continuation application claims priority to PCT/EP2013/071005 filed on Oct. 9, 2013 which has published as WO 2014/060251 A1 and also the German application number 10 2012 218 804.5 filed on Oct. 16, 2012, the contents of which are fully incorporated herein with these references.

FIELD OF THE INVENTION

The present invention relates to an orthosis for stabilizing, guiding and/or correcting a joint.

BACKGROUND OF THE INVENTION

Orthoses have been used for some time as an auxiliary medical means for functionally stabilizing, relieving, guiding and/or correcting joints. For instance, knee orthoses are used, for example, after treating ruptures of the anterior or posterior cruciate ligament, after collateral ligament lesions and in the case of meniscus and cartilage damage.

The orthoses generally have a pair of joint rails each having a first and a second rail portion which are connected to each other in an articulated manner via an orthosis joint at the ends thereof facing each other. The two rail portions can be pivoted relative to each other about a joint axle and can be fixed via fixing means, for example, belts or hook and loop bands, to a respective limb portion, for instance, the upper leg and lower leg.

Although the orthoses are either available in different sizes or are also individually adapted, the joint to be treated with the orthosis often cannot be stabilized or relieved or actively corrected to the desired extent. This may be the case in particular with post-operative or post-traumatic swellings in the joint region and in the event of valgus or varus malalignments of the joint to be treated. In the case of valgus malalignment, the distal limb portion, that is to say, for example, the lower leg, becomes displaced outwards away from the center axis of the limb beyond the normal dimension, whereas the term varus malalignment is intended to be understood to be a displacement inwards. The inadequate stabilization, guiding, relieving or active correction of the joint to be treated or the ligamentous apparatus near the joint can result in a protracted recovery period and where applicable a permanent joint instability.

On the basis of the above-mentioned prior art, an object of the invention is to provide an orthosis and a correction joint for an orthosis which allows improved lateral joint stabilization, guiding, relieving and/or active correction.

The object relating to the orthosis is achieved by an orthosis having the features set out in the first independent patent claim. The correction joint according to the invention for the orthosis has the features set out in a dependent patent claim. The dependent claims relate to advantageous developments of the invention.

SUMMARY OF THE INVENTION

In the orthosis according to the invention, a defined valgus or varus moment can be applied to the joint in accordance with a respective pivot position of the two rail portions relative to each other, that is to say, in accordance with a flexion of the joint treated with the orthosis, as a result of the correction pad (=pressure member) which is arranged for translational movement along the joint axle. Thus, the correction pad can be guided in the direction towards and counter to the joint to be treated, for example, in a neutral position (0° of the joint according to the so-called neutral zero method, the standardized orthopedic evaluation index for joints) or in a bending position (flexion) of the joint, for example, for a knee angle range from 0 to 25° or approximately 30°. In the case of a knee joint, the correction pad can be guided and pressed, for example, against the condylus medialis femoris, that is to say, the distal joint extension of the upper leg bone directed towards the center of the body (valgus moment—correction in the varus sense). The joint to be treated with the orthosis can thereby be generally laterally stabilized, relieved, guided and/or actively corrected in a more effective manner. Furthermore, secondary damage to the joint or to the ligamentous apparatus surrounding the joint can thereby be effectively prevented. The individual recovery period and recovery success can thereby be improved readily and in an economic manner. The correction pad may in particular be a portion of a correction joint of the orthosis, via which portion the two rail portions of the joint rails are connected to each other in an articulated manner.

The axial movement of the correction pad along the joint axle is derived according to the invention from the pivoting movement of the two rail portions in that one of the two rail portions has a cam disc which is connected to that rail portion in a rotationally secure manner and the other of the two rail portions has a rotor (=control member) which adjoins the cam disc. The rotor is rigidly fixed/supported on the other rail portion preferably in an axial direction. The cam disc or the rotor is axially fixed in position on the correction pad so that the correction pad is moved in translation along the joint axle in the event of pivoting of the two rail portions and the resultant relative movement of the cam disc and the rotor which adjoins the cam disc. That is to say, the correction pad carries out a forward travel movement which is orientated along the joint axle of the orthosis in the direction towards and counter to the joint which has been axially malaligned (=valgus or varus malalignments) and which is treated with an orthosis. The relationship between a respective change of an angle which is enclosed by the two rail portions and an axial adjustment movement of the correction pad, which movement is derived therefrom, can readily be adjusted (predetermined) on the basis of a flank pitch of the cam with respect to the joint axle. Furthermore, a (total) travel of the correction pad in an axial direction can be predetermined on the basis of the cam height. The term "cam height" is intended to be understood to be the spacing of the cam tip of the cam from the (axial) nominal height of the cam disc which corresponds to the rest position of the correction pad.

The backward movement of the correction pad from the (active) forward travel end position into the axial rest position thereof can be carried out in a purely passive manner according to the invention. It will be understood that the correction pad may also be able to be moved back alternatively by means of a restoring spring or the like from the forward travel end position into the rest position.

According to the invention, the cam disc may in particular be formed by a cam ring. The cam ring is fixed to the correction pad preferably in a releasable manner. On the one hand, this affords technical advantages in terms of production. On the other hand, the cam ring can readily be changed or, where applicable, also removed without any replacement in the case of wear or also in the case of changing medical requirements. It will be understood that the cam disc may also be formed by a cam plate.

The cam ring may be adjustable in particular in a variably stepless manner on the correction pad in terms of the axial position thereof and in terms of the rotational position thereof on the correction pad. As a result of the selection of the cam profile height, the forward travel end position of the correction pad can be (finely) adjusted and adapted to the individually necessary dimension and in accordance with a respective relative pivot position of the two rail portions in relation to each other in accordance with requirements. Furthermore, the control times can be adjusted by rotating the cam ring. This may be advantageous in particular in the case of a swollen knee or elbow joint. Thus, the correction pad may be pressed counter to the knee joint or the elbow joint, for example, (only) between a bending position of from 20 degrees to the neutral position of the joint to be stabilized. Furthermore, a desired pressing pressure of the correction pad counter to the joint to be stabilized (=valgus or varus moment) can thereby be readily adjusted. In particular, the correction of the orthosis joint may be dispensed with where applicable in the case of the bending, for example, for a knee angle greater than 80° so that lateral relieving of the knee joint is produced whilst sitting.

An excessive loading of the joint which is intended to be stabilized with the orthosis can be prevented according to the invention in that the correcting orthosis allows only a limited movement extent in the joint. This can be achieved in the structurally simplest case in that the cam ring has one or more stops for the rotor.

From structural viewpoints, the orthosis preferably has an annular (rotary) joint.

The correction pad can be arranged in an axially displaceable manner in particular on a bearing member which is engaged round by the (rotary) joint. This allows a coaxial adjustment of the correction pad in relation to the joint axle. In this instance, the bearing member is preferably connected in a rotationally secure manner to one of the two rail portions of the joint rail.

According to a particularly preferred development of the invention, the correction pad has at least one bearing journal which extends through a hole of the bearing member and via which the correction pad is supported (in a sliding manner) in the hole in an axial direction. The hole or the bearing journal may be provided with a PTFE (polytetrafluoroethylene) coating or a PTFE sliding sleeve. According to the invention, the correction pad may also have two or more such bearing journals.

The bearing journal may particularly be provided at one end with a retention portion, on which the cam ring is releasably fixed. The retention portion may in particular be provided with a retention collar for the cam member. It is thereby readily possible to prevent the correction pad from being removed axially or falling out of the hole of the bearing member. In this embodiment, consequently, the retention portion may form a stop for an axial forward travel movement of the correction pad.

The rotor may have according to the invention a ball-bearing roller. It is thereby possible to achieve a particularly robust function of the orthosis with respect to malfunctions. Furthermore, adjustment noises which are disruptive in practice can be reliably prevented.

The correction pad is preferably provided with a padded coating. This is advantageous for wearing comfort and patient safety. Furthermore, pressure points can thereby be combated in a reliable manner.

The wearing comfort and patient safety can be improved even further in that the padded coating on the correction pad is arranged so as to be freely rotatable. This can be brought about according to the invention, for example, by means of a rotary plate or the like which is rotatably supported on the correction pad.

It will be understood that the rail portions may each have fixing means for limb portions, for example, tension belts. For reasons of comfort, the fixing means are preferably provided with hook and loop closures.

The orthosis may advantageously be produced from a light metal, in particular aluminum or an aluminum alloy, or from a carbon fiber material or an unbreakable plastics material. The rail portions may be formed substantially from a formed and bent wire profile.

According to a development of the invention, the orthosis has another joint rail. The additional joint rail may be arranged in particular with spacing from the first joint rail and may also have two rail portions. The joint which is intended to be stabilized with the orthosis can thereby be supported, stabilized and/or corrected at both sides. The additional joint rail may also have according to the invention a correction pad formed in the manner explained above. The correction pads of the two joint rails may be arranged so as to be axially adjustable in the same direction or in opposite directions in particular synchronously or independently of each other.

A correction joint according to the invention for an above-explained orthosis comprises the joint axle and the correction pad which is axially adjustable along the joint axle. The correction joint preferably has two joint portions which can be pivoted relative to each other about the joint axle. The two rail portions of the orthosis may be able to be fixed to the two joint portions, preferably in a releasable manner. Consequently, the correction pad which is axially adjustable along the joint axle is an integral component of the correction joint and can be displaced (in a restricted manner) along the joint axle by means of a relative pivoting of the two joint portions about the joint axle.

BRIEF DESCRIPTION OF THE DRAWINGS

The invention is explained in greater detail below with reference to an embodiment which is illustrated in the drawings, in which.

DETAILED DESCRIPTION OF THE PREFERRED EMBODIMENTS

Figure 1:
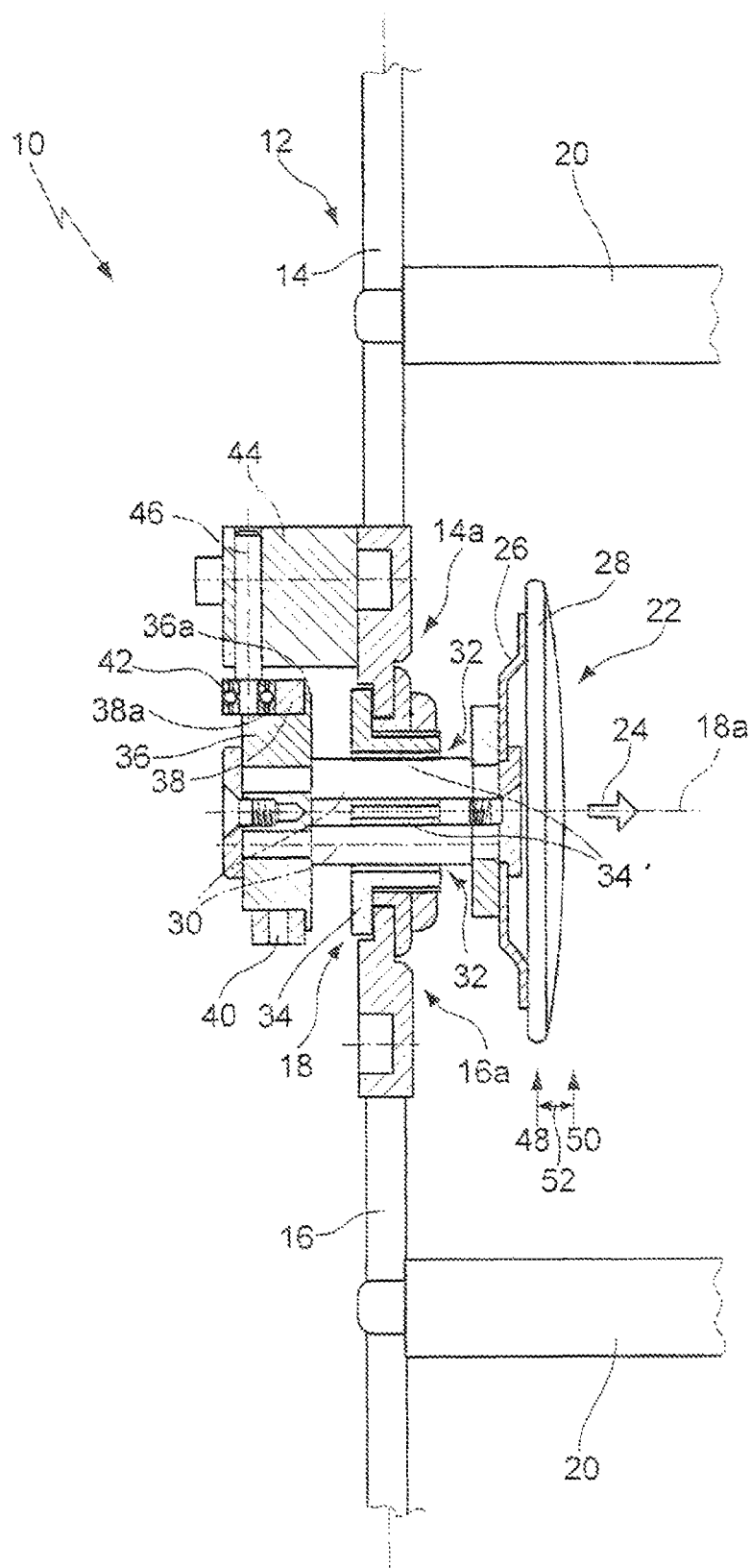
FIG. 1 is a sectional cut-out of an orthosis having a joint rail which has two rail portions which can be pivoted relative to each other, and having a correction pad which is axially adjustable by pivoting the rail portions about the joint axle.

FIG. 1 is a longitudinally sectioned cut-out of an orthosis 10 according to the invention. The orthosis 10 serves to stabilize a knee joint which is not illustrated in greater detail and has a joint rail 12 having a first and a second rail portion 14, 16. The two rail portions are connected to each other by means of a correction joint 18 in the form of a rotary joint at the mutually facing ends 14a, 16a thereof. Fixing means 20 are used to fix the orthosis to the upper leg or lower leg of a person to be treated (not shown). The fixing means 20 are variably adjustable in terms of the axial position thereof on the rail portions 14, 16.

The correction joint 18 has a joint axle (axis) 18a, about which the two rail portions 12, 14 can be pivoted relative to each other. There is arranged on the joint rail 12 a correction pad 22 which can be moved by a pivoting movement of the two rail portions 12, 14 in the rotary joint 18 along the joint axle 20 in the direction towards and counter to the knee joint which is intended to be stabilized, as indicated by the arrow 24. The pressure pad 22 has at one end a rotary plate 26 having a padded coating 28.

The correction pad 22 has two bearing journals 30 which are arranged with spacing from each other and which each have a cylindrical cross-section. The bearing journals 30 extend through holes 32 of an inner bearing member 34 which is engaged round at the peripheral side by the rotary joint 18. The holes 32 of the inner bearing member 34 are each provided with sliding sleeves 34', on which the bearing journals 30 of the correction pad 22 are guided in an axially displaceable manner with sliding play and positive-locking. The sliding sleeves 36 may comprise in particular PTFE (polytetrafluoroethylene) or a PTFE-based material.

A disc-like retention member 36 is arranged at one end on the bearing journals 30. A cam ring 38 is releasably fixed to the retention member 36 by means of a plurality of screws 40. The cam ring 38 is arranged in a state held on the retention member 36 in a rotationally secure and axially non-displaceable manner and can be arranged so as to be steplessly variable in terms of the rotary position thereof relative to the joint axle 18a and in terms of the axial position thereof on the retention member 36 by the screws 40 being loosened. As can be seen in FIG. 1, the cam ring 38 adjoins a collar 36a of the retention member 36 in this instance.

Figure 3:
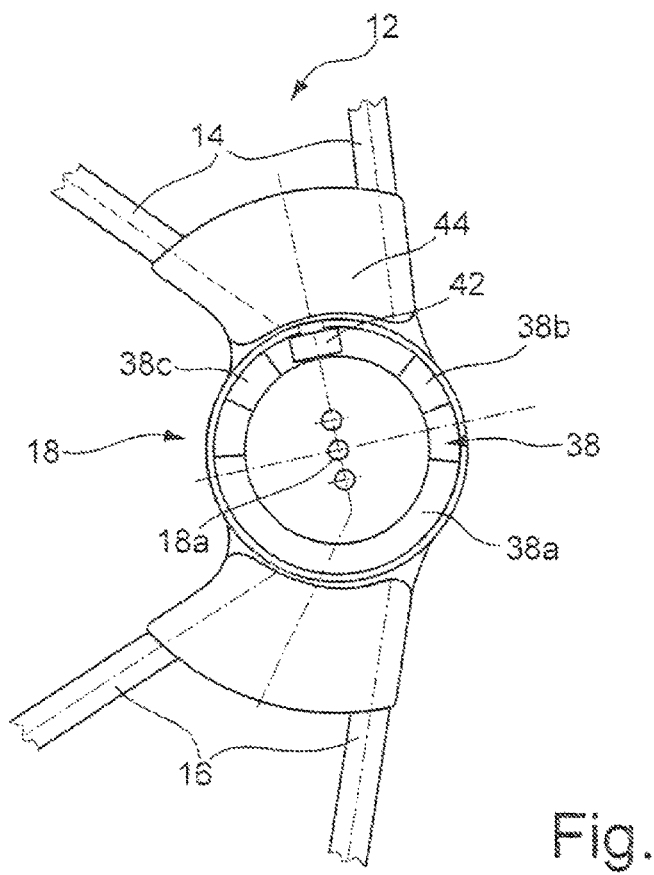
FIG. 3 is a side view of a cut-out of the orthosis from FIG. 1.
Figure 4:
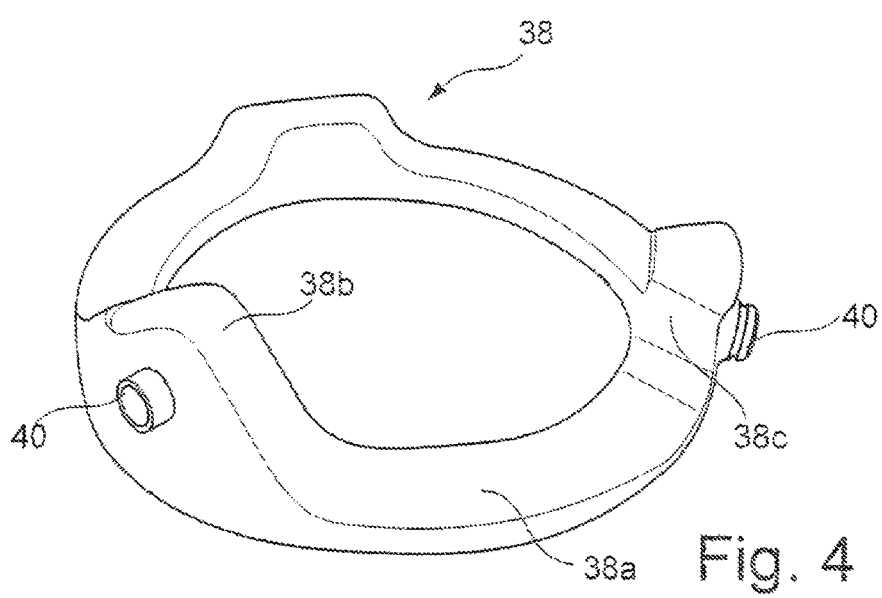
FIG. 4 is a perspective cut-out of a cam ring of the orthesis according to FIG. 1, by means of which cam ring the pressure member is coupled in terms of movement to the two rail portions of the joint rail.

The cam ring 38 has a cam disc 38a, that is to say, a control cam having a cam (not shown) which is illustrated in greater detail in FIGS. 3 and 4. In other words and as can be seen in FIG. 4, the cam ring 38 has a changing/variable cam surface 38a.

A rotor 42 adjoins the cam disc 38a. The rotor 42 is arranged on a bearing block 44 of the first rail portion 14 and is in the form of a ball-bearing roller which can be freely rotated about a roller axis 46.

When the two rail portions 14, 16 are pivoted in the rotary joint 18, consequently, the rotor 42 rolls on the cam disc 38a which is guided under the rotor 42. As soon as the rotor 42 is guided against the cam (not shown), the cam ring 38 is moved together with the correction pad 22 out of the rest position 48 shown here along the joint axle 18a of the rotary joint 18 in the direction 24 towards and counter to the knee to be stabilized.

A forward travel end position of the correction pad 22 is designated 50. In this instance, the correction pad 22 has a travel 52 of approximately 10 mm in this instance. The travel 52 corresponds to the axial spacing between the neutral position 48 and the forward travel end position 50 of the correction pad 22.

Figure 2:
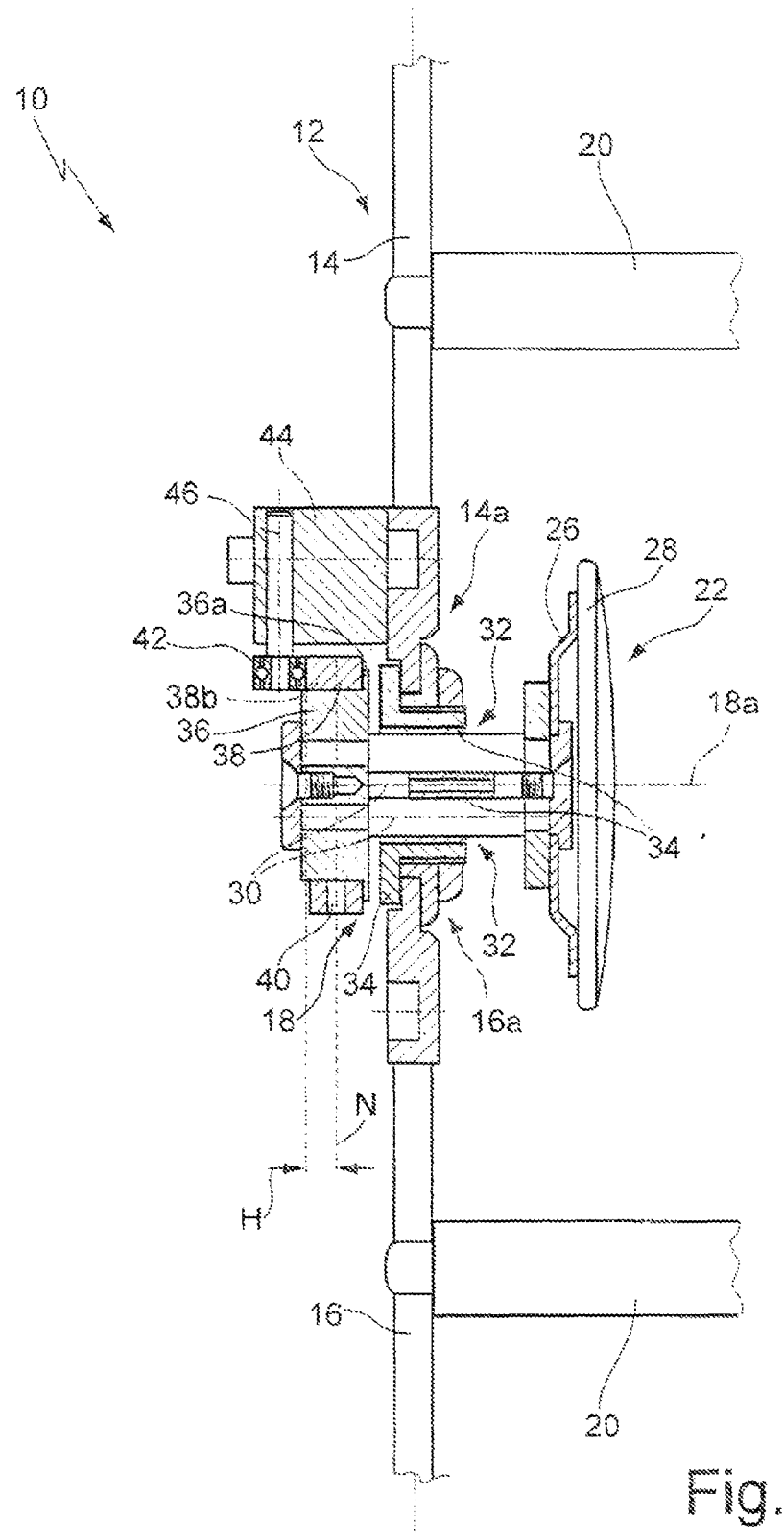
FIG. 2 is a sectional cut-out of the orthosis from FIG. 1 with a correction pad arranged in a forward travel end position.

FIG. 2 shows the orthosis 10 with the correction pad 22 adjusted into a forward travel end position 50. The two rail portions 14, 16 are not angled relative to each other in the embodiment shown here. The rotor 42 adjoins the cam 38b of the cam disc 38a of the cam ring 38. The cam has, in relation to the nominal height N of the cam disc, a cam height H which corresponds to the travel 52 of the correction pad 22. The correction pad 22 adjoins, in the forward travel end position 50 shown, the knee joint which is intended to be stabilized with the orthosis, preferably in the region of the medial or lateral condyle.

FIG. 3 is a side view of a cut-out of the orthosis 10 with the correction pad removed. The cam ring 38 with the rotor 42 which is positioned thereon at the front side can clearly be seen. The rail portions 14, 16 are substantially constructed as profiled light metal struts. The rail portions 14, 16 may also be formed from a different material, in particular from a carbon fiber material.

FIG. 4 is a perspective cut-out view of the cam ring 38. The cam disc 38a comprises the cam 38b, by means of which the correction pad can be axially adjusted. A stop 38c for the rotor 42 serves to delimit the movement extent of the two rail portions 14, 16 in the rotary joint 18 (FIG. 1).

The above-described orthosis is particularly suitable for all medical indications in which it is necessary to guide, stabilize, relieve and/or correct the knee joint or elbow joint or to relieve the joint, such as, for example, in the case of a higher-grade and/or complex instability of the knee joint, in meniscus injuries, cartilage damage and for functional preoperative and/or post-operative care, in particular after ruptures of the ligamentous apparatus with or without axial malalignments. The orthosis has a correction joint which is in the form of a rotary joint and which has a first and a second rail portion which can be pivoted about a joint axle relative to each other. The correction joint has a correction pad which can be moved by means of an adjustment movement which is derived from the pivoting movement of the two rail portions along the joint axle in the direction towards and counter to the joint which is intended to be stabilized/corrected.

What is claimed is:

1. An orthosis for stabilizing, guiding and/or relieving a joint, the orthosis comprising:
    a joint rail having a first and a second rail portion which can be pivoted relative to each other about a common joint axle;
    a correction pad configured to move by a relative pivoting of the first and second rail portions along the joint axle in a direction towards and counter to the joint to be stabilized;
    wherein one of the first or second rail portions has a cam disc, the cam disc having a variable surface;
    wherein the other of the first or second rail portions has a rotor which is guided on the variable surface of the cam disc; and
    wherein the cam disc or the rotor is axially fixed in position on the correction pad.

2. The orthosis according to claim 1, wherein the joint rail has a bearing member which is arranged on the joint axle and on which the correction pad is supported in an axially displaceable manner.

3. The orthosis according to claim 2, wherein the correction pad has one or more bearing journal(s) which is/are slidingly supported in holes of the bearing member.

4. The orthosis according to claim 3, wherein the bearing journal(s) are cylindrical.

5. The orthosis according to claim 3, wherein the bearing journals are provided at one end with a retention portion, on which the cam ring is releasably fixed.

6. The orthosis according to claim 1, wherein the cam disc is formed by a cam ring which is fixed to the correction pad in a releasable manner.

7. The orthosis according to claim 6, wherein the cam ring can be arranged on the correction pad so as to be variable in terms of the axial position thereof and in terms of the rotational position thereof relative to the correction pad.

8. The orthosis according to claim 6, wherein the cam ring has one or more stops for the rotor.

9. The orthosis according to claim 1, wherein the rotor has a ball-bearing roller.

10. The orthosis according to claim 1, wherein the correction pad has a rotary plate having a padded coating.

11. The orthosis according to claim 1, including another joint rail having a first and a second rail portion.

12. An orthosis for stabilizing, guiding and/or relieving a bodily joint of a person, the orthosis comprising:
   a first rail portion pivotably attached to a second rail portion about a common joint axis, either rail portion attachable to an upper leg or a lower leg of the person;
   a correction pad translatably attached relative to the first rail portion aligned along the joint axis, the correction pad configured to be disposed on an inside portion of the orthosis facing towards the bodily joint of the person;
   a cam ring attached to the correction pad, the cam ring having a variable surface, where the correction pad and cam ring are translatable in a direction aligned with the joint axis;
   a rotor rotatably attached to the second rail portion, wherein the rotor abuts and engages the variable surface of the cam ring;
   wherein a pivotable movement of the first rail portion in relation to the second rail portion creates a translation movement of the correction pad along the joint axis due to the rotor engaging the variable surface of the cam ring.

13. The orthosis according to claim 12, including a cam ring retention member attached to the correction pad, wherein the cam ring is rotatably adjustable and securable in relation to the cam ring retention member.

14. The orthosis according to claim 13, wherein the cam ring comprises at least one female-threaded fastener hole configured to receive a fastener thereby securing the cam ring to the cam ring retention member.

15. The orthosis according to claim 12, wherein the cam ring is rotatably adjustable relative to the first rail portion.

16. The orthosis according to claim 12, wherein the cam ring can be arranged in relation to the correction pad so as to be variable in terms of the rotational position thereof relative to the correction pad.

17. The orthosis according to claim 12, wherein the rotor has a ball-bearing roller.

18. The orthosis according to claim 12, wherein the correction pad has a rotary plate having a padded coating.

19. The orthosis according to claim 12, wherein the cam ring comprises one or more stops for the rotor preventing passage of the rotor beyond the stop.

20. An orthosis for stabilizing, guiding and/or relieving a bodily joint of a person, the orthosis comprising:
   a first rail portion attachable to either an upper leg or a lower leg of the person;
   a second rail portion attachable to the other of the upper leg or the lower leg of the person;
   a mechanical joint pivotably coupling the first rail portion to the second rail portion, where the first rail portion can be pivoted relative to the second rail portion about a common joint axis that is generally aligned with the bodily joint of the person;
   a correction pad translatably attached relative to the first rail portion through the mechanical joint aligned along the joint axis, the correction pad configured to be disposed on an inside portion of the orthosis facing towards the bodily joint of the person;
   a cam ring attached to the correction pad, the cam ring disposed on an outside portion of the orthosis, where the cam ring is rotatably adjustable and securable relative to the first rail portion, the cam ring having a variable surface;
   wherein the correction pad and cam ring are translatable relative to the first and second rail portions in a direction aligned with the joint axis;
   a rotor rotatably attached to the second rail portion, wherein the rotor abuts and engages the variable surface of the cam ring;
   wherein a pivotable movement of the first rail portion in relation to the second rail portion creates a translation movement of the correction pad along the joint axis due to the rotor engaging the variable surface of the cam ring.

* * * * *